(12) United States Patent
Brand

(10) Patent No.: US 8,492,735 B2
(45) Date of Patent: Jul. 23, 2013

(54) METHOD FOR OPTIMIZATION RADIOTHERAPY PARTICLE BEAMS

(75) Inventor: Matthew Brand, Cambridge, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 243 days.

(21) Appl. No.: 12/788,437

(22) Filed: May 27, 2010

(65) Prior Publication Data

US 2011/0291028 A1   Dec. 1, 2011

(51) Int. Cl.
*A61N 5/10* (2006.01)
*H01J 37/08* (2006.01)

(52) U.S. Cl.
USPC ................. 250/492.22; 250/492.1; 378/65

(58) Field of Classification Search
USPC ............. 250/492.1, 492.21, 492.22, 492.23, 250/492.3, 526; 378/1, 2, 65, 92, 97, 98, 378/210, 64, 901
See application file for complete search history.

(56) References Cited

U.S. PATENT DOCUMENTS

| | | | |
|---|---|---|---|
| 6,029,079 A * | 2/2000 | Cox et al. | 600/407 |
| 6,546,073 B1 * | 4/2003 | Lee | 378/65 |
| 6,714,620 B2 * | 3/2004 | Caflisch et al. | 378/65 |
| 6,741,674 B2 * | 5/2004 | Lee | 378/65 |
| 6,882,702 B2 * | 4/2005 | Luo | 378/65 |
| 7,046,762 B2 * | 5/2006 | Lee | 378/65 |
| 7,519,150 B2 * | 4/2009 | Romesberg et al. | 378/65 |
| 8,218,725 B2 * | 7/2012 | Muller et al. | 378/65 |
| 2002/0106054 A1 * | 8/2002 | Caflisch et al. | 378/65 |
| 2005/0207531 A1 * | 9/2005 | Dempsey et al. | 378/65 |
| 2010/0177872 A1 * | 7/2010 | Muller et al. | 378/65 |
| 2011/0121195 A1 * | 5/2011 | Harada et al. | 250/396 ML |
| 2011/0142316 A1 * | 6/2011 | Wang et al. | 382/131 |
| 2011/0191085 A1 * | 8/2011 | Jaffray et al. | 703/11 |
| 2011/0248188 A1 * | 10/2011 | Brusasco et al. | 250/492.1 |

* cited by examiner

*Primary Examiner* — Bernard E Souw
(74) *Attorney, Agent, or Firm* — Dirk Brinkman; Gene Vinokur

(57) ABSTRACT

Radiation doses are optimized by providing a model of the set of beams and a target dose in normalized forms. A Gram matrix is determined from the model. The target dose is subsampled to determine initial intensity values for the set of beams. Then, the following steps are iterated until convergence. A very small positive value, $0<\epsilon\ll 1$, is added to each intensity value to ensure the intensity value is greater than zero. Each intensity value is multiplied by the Gram matrix to determine a product, which is divided element-wise into the normalized target dose to determine corresponding ratios. If the ratios are all close to 1, within a numerical error tolerance, the intensity values of the set of beam are output. Otherwise, the intensity values are multiplied by the ratios before a next iteration.

9 Claims, 1 Drawing Sheet

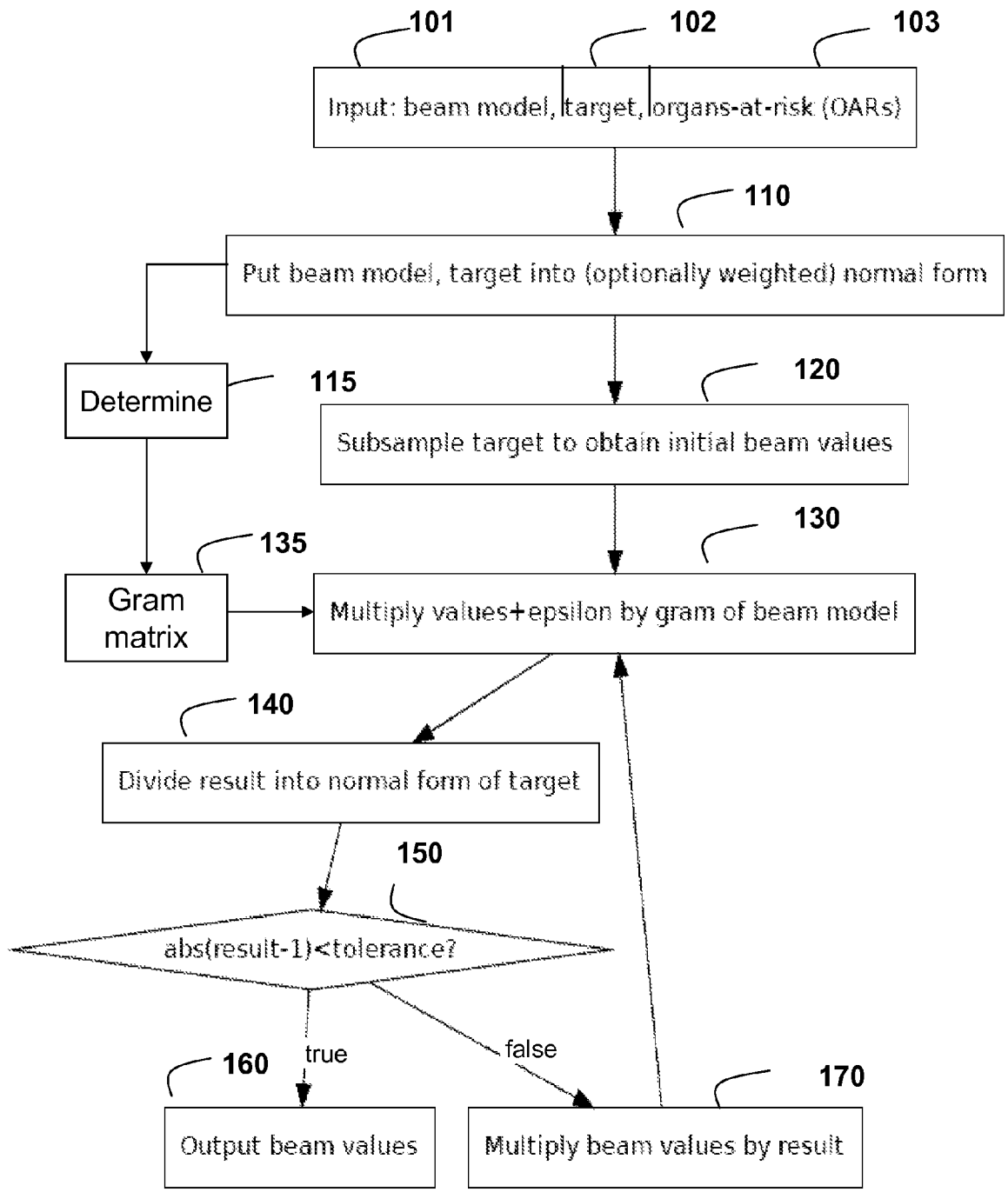

METHOD FOR OPTIMIZATION RADIOTHERAPY PARTICLE BEAMS

FIELD OF THE INVENTION

This invention relates generally to radiotherapy, and more particularly to optimizing radiation doses delivered to tissue by a set of particle beams.

BACKGROUND OF THE INVENTION

In a simplest version of radiation dose optimization, a dose matrix $A \in \Re^{n \times m}$ indicates a radiation target dose delivered by a set of m beams in n voxels. Here, the voxels represent small cubes (mm$^3$) in a volume of tissue. A vector of nonnegative beam weights $x \in \Re^m$ linearly combines the beams to yield a vector $$y = Ax \in \Re^n$$

of cumulative voxel radiation dosages. Typically, the dose matrix A is relatively tall (n>>m), and sparse. The problem is to determine beam weights that guarantee no underdoses and minimal overdoses, given a target dosage pattern $b \in \Re^n$. This is a linear program (LP):

$$\min_{x} \|Ax - b\|_1 \text{ such that } Ax \geq b, x \geq 0. \quad (1.1)$$

A small problem (m~10$^3$ beams and n~2m voxels) can currently be solved in roughly one second on a 2 GHz Pentium 4 processor. However, the LP solution time generally scales as the cube of the problem size, and so that method is presently impractical for practical clinical problems with much larger sizes.

LP and second-order cone (SOCP) methods are attractive because they lend themselves to formulations that minimize dose delivery errors. However, problems are limited to just a few thousand variables and constraints, and require hours to solve. For that reason, the problem prefers an $L_2$ norm in an objective function, i.e., minimize the sum squared error while disallowing underdoses. This is a least-squares with inequalities problem (LSI):

$$\min_{x} \|Ax - b\|_2^2 \text{ such that } Ax \geq b, x \geq 0. \quad (1.2)$$

The LSI can be justified as optimizing an upper bound on the LP. Minimizing sum-squared overdose gives solutions that are slightly smoother, but not as safe because the overdose is larger. This LSI is a particularly well-behaved instance of a quadratic program (QP), assuming the matrix A has a full row rank, and the QP is strictly convex. Herein, LSI and QP are used interchangeably.

Fast Approximate Methods

In the prior art, it is common to use methods that avoid the underdosing constraint and simply seek to reduce a sum squared error $$\|Ax - b\|_2^2,$$

or a weighted sum squared error $$\|W(Ax - b)\|_2^2.$$

Due to the size of the problem, solutions are computed iteratively via gradient, conjugate gradient, or quasi-Newton methods, or preferably, a limited memory Broyden-Fletcher-Goldfarb-Shanno (L-BFGS) method. To avoid physically impossible solutions, those methods are usually modified so any beam weight $x_i$ that is negative is reset to zero. That is not guaranteed to find an optimum or avoid underdoses, but appears to work well enough for clinical use.

More principled methods, such as gradient projection, can guarantee non-negativity and optimality, but increase processing time and are thus slower. For this reason, parallel solutions on graphic processor units (GPU) are sometimes used that solve small problems in a matter of seconds.

SUMMARY OF THE INVENTION

The embodiments of the invention provide a method for optimizing radiation doses delivered by a set of particle beams. The method uses a family of very fast multiplicative updates for solving nonnegative least-squares (NNLS) problems and a special class of quadratic programs (QP). Through problem transformations, the iterative updates can solve least distance problems (LDP), least-squares inequality problems (LSI), and general quadratic programs (QP).

The motivating application is radiation dose optimization, which is a linear program (LP) so large that the constraint matrix cannot be stored in a practical memory.

The method upper-bounds the LP's L1 objective with an L2 norm to obtain the QP, and develops a variety of exact and approximate solutions via multiplicative iterations.

BRIEF DESCRIPTION OF THE DRAWINGS

FIG. 1 is a flow diagram of the method according to embodiments of the invention.

DETAILED DESCRIPTION OF THE PREFERRED EMBODIMENTS

The embodiments of the invention provides a considerably faster method that guarantee squared-error optimality and non-negative weights for radiotherapy particle beams.

For "pencil beam" treatment, there are roughly n~10$^6$ voxels, and m~10$^4$ beams. Consequently, the compute time is determined mostly by the number of voxels, and it is desirable to reformulate the problem in a way that minimizes voxel-based calculations. The steps of the method can be performed in a processor connected to a memory and input/output interfaces as known in the art.

As shown in FIG. 1, input to the method includes a beam model 101, a target dose 102, and locations of organs at risk (OAR) 103.

The first step 110 determines a normalized model and a normalized target dose.

A Gram matrix $Q \doteq A^T A \in \Re^{m \times m}$ 135 of the beam model is determine 115 beforehand, where $^T$ is the transpose operator. Then, the same transform is applied to the target dose to obtain $h \doteq A^T b \in \Re^m$. The Gram matrix of a set of vectors in an inner product space is the Hermitian matrix of the inner products.

The target dose is subsampled 120 to determine initial intensity values for the set of beams.

For now, an inequality constraints is ignored. The objective function is rewritten as an unconstrained least-squares (LS) problem $$x^* = \min_{x} \|Ax - b\|_2^2 = \min_{x} \frac{1}{2} x^T Q x - h^T x, \quad (2.1)$$

that is two orders of magnitude smaller than the original LSI. Note that there is some loss of numerical precision in the normal form, but that is mitigated by the sparsity of the dose matrix A.

The unconstrained least-squares problem replaces the hard inequality constraint Ax≈b with a soft squared-error constraints Ax≧b. Because this problem is non-negative (A, b≧0) and over-constrained (n>>m), the LS-optimal solution has two deficiencies: some LS-optimal beam weights will be very negative ($X_i$<0); and some voxels will be underdosed ($A_ix$<$b_i$).

The method according to the invention completely eliminates the first problem of the negative beam weights. Given a non-negative least-squares (NNLS) problem $$\min_x \|Ax - b\|_2^2 \text{ s.t. } x \geq 0, \quad (2.2) \qquad (2.2)$$

let $$Q \doteq A^TA, h \doteq A^Tb, \lfloor x \rfloor = \max(x,0), \lceil x \rceil \doteq \max(-x,0).$$

A multiplicative update 130

$$x \leftarrow \text{diag}(\lfloor h \lceil Q \rceil x \rfloor)\text{diag}(\lfloor Q \rfloor x)^{-1} x \qquad (2.3)$$

is a contraction that, for any positive h and positive definite Q, converges to the optimum from any positive weight vector x>0. This equation multiplies each element of x by a ratio that is related to the gradient. In practice, convergence is achieved when all of the multipliers are equal to 1, within a numerical error tolerance 150. In this case, the intensity values of the set of beams are output 160. if true. Otherwise, if false, the intensity values are multiplied 170 by the result before the next iteration.

In the context of dose optimization, $$\forall_{ij}, Q_{ij} \geq 0, h_i > 0,$$

thus the iteration can be simplified to a single matrix-vector product, then one multiplies 130 and divides 140 per beam weight, making it amenable to fine-grained parallelization. The cost of the iteration is dominated by the number of nonzero entries in the Gram matrix Q, which are the number of beam-pairs that have non-vanishing overlap.

The second problem of underdosing arises because least-squares solutions spread error smoothly, with the consequence that voxels on the boundary of tissue volume to be treated are underdosed as a way of minimizing the overdose to adjoining voxels corresponding healthy tissue. For NNLS problem in Equation (2.2), avoiding underdoses is only a soft constraint. There are several heuristics that strengthen that constraint without making the problem fundamentally more difficult to solve:

(1) Explicitly penalize variance in the dosage to the voxels to be treated by by adding $\tau A^T S(I-1/t1)S^T A$ to Q, where S is a binary matrix that selects these voxels, I is the identity matrix, 1 is a matrix of all 1's, and t is the number of such voxels, and τ is a weighting term that balances dosage error against variance;

(2) Reweight the sum of squared errors so that dosage errors at boundary voxels are much more heavily penalized than elsewhere, and similarly underweight voxels outside the treatment volume. That is, there is some voxel error weighting vector w, and set $$Q = A^T\text{diag}(w)A \text{ and } h = A^T\text{diag}(w)b.$$

(3) Q=A(diag(w)A and h=A(diag(w)b; and
(4) Modify the target tissue volume is surrounded by a "skirt" of positive values whose decay approximately matches the decay profile of a beam.

Exact Solutions

If avoiding underdoses is set as a hard constraint, then the problem becomes much more formidable as it becomes necessary to set the calculations in the vastly larger space of voxel dosages, and work with rank-deficient matrices; both these conditions slow the convergence of iterative solvers. On the other hand, no heuristics are needed.

This section considers reformulations of the original LSI/QP that guarantee no underdose, and provides solutions via multiplicative updates.

Minimize Total Dosage

It might be desirable to minimize the total dosage $\|Ax\|_1$ subject to the no-underdose constraint. Without loss of generality, the nonegative A has unit column sums, so that $\|Ax\|_1 = \|x\|_1$. Because $\|x\|_2 \geq \|x\|_1$, an upper bound on the total dosage can be minimized in the following least-distance problem (LDP):

$$\min_x \|x\|_2 \text{ s.t. } Ax \geq b, x \geq 0,$$

which is known to have an equivalent NNLS form $$\min_{u,v} \left\| \begin{bmatrix} A & b \\ I & 0 \end{bmatrix}^T \begin{bmatrix} u \\ v \end{bmatrix} - [0, \ldots, 0, 1]^T \right\|_2^2 \text{ s.t. } u, v \geq 0,$$

which can be solved via the NNLS iteration. The LDP and NNLS optima are related by $$(1-b^T u^*)x^* = A^T u^* + v^*,$$

provided the original constraints are consistent, otherwise the right hand side is zero. Note that this LDP allows larger overdoses than the original QP in Equation (1.2) because the objective $\|x\|+2$ favors smoother solutions. Also, the LDP is very large, with dim(u)+dim(v)=#voxels+#beams unknowns. However, this does no allow one to exploit the sparsity of the matrix A for speed.

Rotate the LSI into LDS Form

The original LSI can be solved exactly by transformation into a slightly more complex LDP by making a change of variable to z such that $$\|Ax-b\|_2^2 = \|z\|_2^2.$$

Then, the LSI can be rewritten as an equivalent LDP. A "thin" QR decomposition of A is UR=A where U is unitary and R is an upper triangular and nonnegative on the diagonal. The QP is rewritten with a $L_2$ norm-preserving change of variable $z \doteq U^T(Ax-b)=Rx-U^T b$ to obtain min $$\min_z \|z\|_2 \text{ s.t. } Cz \geq d$$

with $$C \doteq \begin{bmatrix} U \\ R^\dagger \end{bmatrix}, d \doteq \begin{bmatrix} (I - UU^\top) \\ -R^\dagger U^\top \end{bmatrix} b,$$

† denoting a pseudo-inverse.

The corresponding NNLS is $$\min_{u,v} \|[C\ d]^\top u - [0, \ldots, 0, 1]^\top\|_2^2 \text{ s.t. } u \geq 0$$

with optima related by $(1 - d^T u^*) \cdot z^* = C^T u^*$, and then $x^* = R^\dagger(z^* + U^T b).$ The corresponding multiplicative update solves the dosage problem with no underdose, no negative weights, and minimal sum-squared overdose. However, whereas the previous LDP/NNLS was sparse, this NNLS is dense, which requires considerably more calculation per iteration. Also, there is a loss of precision due to the fact that the problem is twice transformed.

Solve the QP Dual

Given a strictly convex quadratic program in primal form, $$x^* = \min_x \frac{1}{2} x^\top P x - q^\top x \text{ such that } Ax \geq b, \quad (3.1)$$

the Lagrange dual of a quadratic program takes the form $$\lambda^* = \min_\lambda \frac{1}{2} \lambda^\top Q \lambda - h^\top \lambda \text{ such that } \lambda \geq 0 \quad (3.2)$$

with $Q = AP^{-1}A^\tau$ and $h = b - AP^{-1}q$.

The primal and dual optima are related by $x^* = P^{-1}(q + A^T\lambda)$, and the dual can be solved by the NNLS iteration. Note that $x \geq 0$ is not ensured unless explicitly coded into the constraint $Ax \geq b$. To specialize this to the dosage optimization LSI/QP in Equation (1.2), set $Q \doteq A'(A^\tau A)^{-1} A'^\tau$, and $h \doteq b' - Ob'$, solve, $x^* = (A^\tau A)^{-1} A'^\tau (b' + \lambda^*).$ Here, $A' \doteq [A^\tau, I]^\tau$, and $b' \doteq [b^\tau, 0]^\tau$ to incorporate the constraint $x \geq 0$. The inverse $(A^T A)^{-1}$ can be calculated efficiently using the convolution decomposition described above. Care must be taken because $(A^T A)$ is likely to be poorly conditioned.

Solve a Reduced Primal QP Via Iteration

An error in the radiation doses is reduced to rectangular subregions of the target dose by adding auxiliary matrix-vector products, representing extra penalties for missing dose values within the subregions, to the denominators of the ratios.

Specifically, consider restricting the constraint set of the original QP to forbid underdoses at only $k \leq 2$ m voxels, e.g., those voxels on the boundary, and that are farthest from beam centers. For the restricted QP with nonnegative Q, h, A, b and for all i, $Q_{ii} > 0$, $h_i > 0$, auxiliary matrix-vector products are provided $\lambda \leftarrow \text{diag}(A''x)^{-1}\text{diag}(b'')\lambda$ $x \leftarrow \text{diag}(Qx)^{-1}\text{diag}(h + A'''\lambda)x,$ where b" is a subset of b corresponding to the k constrained voxels, and A" is the corresponding subset of the rows of the dose matrix A.

The auxiliary matrix-vector products $\lambda \in \mathfrak{R}^k$ contains dual variables, also known as shadow prices, which are positive in the solution when a constraint is active and zero otherwise. In constrained optimization, as herein, the shadow prices represent a change in the objective value of the optimal solution of the optimization problem obtained by relaxing the constraint by one unit.

This method can also be used to impose hard constraints on the maximal or minimal cumulative dosage to any set of voxels. The update for $\lambda$ can be changed to small step along the gradient of the Lagrangian with respect to $\lambda$.

Computational Details for Iterations

Multiplicative iteration procedures have linear complexity and converge at a linear rate from anywhere in a positive cone. A constant number of bits of precision are gained in each iteration. Multiplicative updates have the advantage that all normegativity constraints are implicitly enforced. However it is possible that numerical error will round a very small intensity value to zero, after which the intensity remain "stuck" at zero boundary.

Therefore, in step 130, a very small positive value, $0 < \epsilon \ll 1$ is added to each intensity value to produce a positive intensity value before the multiplying. This allows the iterations to escape the zero boundary. The per-variable updates can be executed in a vector-parallel fashion as a message-passing procedure, or the updates can be executed sequentially, in which case the update of the beam weight $x_i$ benefits from the update of the weight $x_j$ whenever $Q_{ij} \neq 0$. This results in a somewhat faster convergence.

Early termination is recommended in this application because it is not unusual to administer doses with ±2.5% error, so any precision in the beam weights x beyond 7 bits is wasted.

Computational Details for Dose Optimization

Separable Convolutions

Forming the matrix $Q = A^T A$ is typically the most time consuming operation in these schemes. Often, it can be avoided entirely. The key insight is that $Q_{ij}$ is the inner product of two beams, and thus can be computed by a convolution. This can be exploited in the simplest possible beam model. The beam is the outer product of an xy planar Gaussian function with a standard deviation $\sigma$, and a Bragg curve in z. Consequently, the 3D convolution of two beams offset by p, q, r decomposes into an outer product of 1D convolutions $$\int_{z_{min}}^{z_{max}} \int \int \mathcal{B}(z - r)\mathcal{B}(z)\mathcal{N}(x - p, y - q; \sigma)\mathcal{N}(x, y; \sigma) dx\, dy\, dz =$$

$$\int_{z_{min}}^{z_{max}} \mathcal{B}(z - r)\mathcal{B}(z) dz \cdot \frac{1}{2}\left(\exp - \frac{p^2 + q^2}{4\sigma^2}\right) \propto$$

$$(\mathcal{B} * \mathcal{B})(r) \cdot \mathcal{N}(p; \sqrt{2}\sigma) \cdot \mathcal{N}(q; \sqrt{2}\sigma).$$

In the above Equation, $\overleftarrow{\mathcal{B}}$ is simply $\mathcal{B}$ reversed. Consequently, the entries of the matrix Q matrix are the outer product of an auto-convolved Bragg curve and two 1D Gaussian functions $Q = Q_B \otimes Q_G \otimes Q_G.$ This structure can be exploited to rapidly determine the action of Q on x via a reshaping identity $(C \otimes D)x = \text{vec}(D^T \text{vec}_{rows(D)}(x)C).$ Using this identity once for each outer product reduces the total number of scalar multiplications by a factor of rows $(B_G)^2$, i.e., the number of beam spots in a plane. As an advantage, for a volume of x+y+z voxels, only the x+y+z entries in the vectors $Q_B$, $Q_G$, $Q_G$ are used, instead of the $(xyz)^2$ entries in the Gram matrix Q.

By the same logic, the vector $h=A^\tau b$ can be formed efficiently by sequentially convolving the 3D target dose b along the x and y axes with 1D Gaussian functions, then along the z axis with the Bragg curve.

Weighted Error in Bounded Domains

Note that the Gaussian convolution spans the entire infinite xy plane, which implies that one is the minimizing squared error everywhere. Because the target dosage is implicitly zero almost everywhere, infinite span contributes to roll-off at the boundary of the target. The contribution appears to be vanishingly small, but in some cases, the integration is bounded to some small volume $$\int_{z_{min}}^{z_{max}} \int_{y_{min}}^{y_{max}} \int_{x_{min}}^{x_{max}} B(z-r)B(z)\mathcal{N}(x-p, y-q; \sigma)\mathcal{N}(x, y; \sigma)\,dx\,dy\,dz =$$

$$\int_{z_{min}}^{z_{max}} B(z-r)B(z)dz \cdot \frac{1}{8}\left(\exp - \frac{p^2+q^2}{4\sigma^2}\right)$$

$$\left(\Phi\left(\frac{x_{max}}{\sigma} - \frac{p}{2}\right) - \Phi\left(\frac{x_{min}}{\sigma} - \frac{p}{2}\right)\right)\left(\Phi\left(\frac{y_{max}}{\sigma} - \frac{q}{2}\right) - \Phi\left(\frac{y_{min}}{\sigma} - \frac{q}{2}\right)\right) \propto$$

$$(\mathcal{B} * \mathcal{B})(r) \cdot \mathcal{N}(p; \sqrt{2}\sigma)\left(\Phi\left(\frac{x_{max}}{\sigma} - \frac{p}{2}\right) - \Phi\left(\frac{x_{min}}{\sigma} - \frac{p}{2}\right)\right) \cdot \mathcal{N}(q; \sqrt{2}\sigma)$$

$$\left(\Phi\left(\frac{y_{max}}{\sigma} - \frac{q}{2}\right) - \Phi\left(\frac{y_{min}}{\sigma} - \frac{q}{2}\right)\right),$$

where $\Phi(\bullet)$ is an error function. Again, this is a nonnegative outer product.

Weighted Error

An error in the radiation dose is reduced to rectangular subregions of the target dose by adding auxiliary not in spec Second formula of Weighted Error section matrix-vector products, representing extra penalties penalties for missing dose values within the subregions, to the denominators of the ratios.

The bounded form of the Gram matrix Q becomes useful when minimizing the weighted squared error $\|\text{diag}(w)Ax - \text{diag}(w)b\|_2$. To work with the normal form, a weighted products $$Q \doteq A^\tau \text{diag}(w)^2 A \text{ and } h \doteq = A^\tau \text{diag}(w)b.$$

Unfortunately, most choices of w pre-empt the use of outer product decompositions to construct Q. But in some useful cases, the outer product can be obtained by partitioning the weighted Q into two matrices $$Q = A^\tau A + A^\tau(\text{diag}(w)^2 - I)A,$$

For example, to uniformly overweight some bounding box, e.g., around organs at risk, by $w_i = c > 1$, the second summand is simply a bounded-integration Q matrix, as described above, multiplied by $c^2 - 1$. To overweight a small number of individual pixels, let $$w_i' = \sqrt{w_i^2 - 1},$$

and let W' contain the nonzero columns of diag(w'), so that the second summand can be written as $$A^\tau(\text{diag}(w)^2 - I)A = (A^\tau W')(A^\tau W')^\tau.$$  i.

The columns of $A^T W'1$ can be pre-calculated the same way as h, and its action on x is most efficiently calculated as $$(A^\tau W')((A^{\tau W'})^\tau x).$$

Note that to use the outer product multiplication, the action of the two summands on x and sum the result are determined separately.

EFFECT OF THE INVENTION

The embodiments of the invention use a quadratic programs (QP) to solve the extremely large and complex problem of optimizing particles beams for radiotherapy treatment.

QPs are ubiquitous in network optimization, machine learning, logistics, control, and many other applications. They are particularly useful when estimating quantities, often denominated in joules, time, or money, that cannot go negative.

Methods for solving QPs have been developed intensively since WW2, with at least one Nobel Prize is connected to work in the area (Harry Markowitz—1990. Nowadays there is a large collection of powerful methods, but problem sizes have been getting out of hand.

The invention provides a new and remarkably simple fixpoint that solves QPs in linear time, linear space, with a linear rate of convergence. This turns out to be of particular useful for optimizing particle beams, where QPs can have $>10^4$ variables and $>10^6$ constraints.

Due to its simplicity, the fixpoint is very fast and parallelizable. The priort QPs require hours to solve the problem. The method as described herein can sove the problem at video frame-rates.

Although the invention has been described by way of examples of preferred embodiments, it is to be understood that various other adaptations and modifications may be made within the spirit and scope of the invention. Therefore, it is the object of the appended claims to cover all such variations and modifications as come within the true spirit and scope of the invention.

I claim:

1. A method for optimizing radiation doses delivered by a set of beams, wherein each beam is a radiotherapy particle beam, comprising the steps of:
   providing a dose matrix A indicating a dose delivered to m target voxels by n beams;
   providing a target dosage pattern vector b required for a radiotherapy; and
   determining, using a processor, a non-negative beam weights vector x that specifies individual intensities of the beams of radiation for radiating a target according to the target dosage pattern, such that underdoses and overdoses of the radiation are minimized, wherein the determining comprises:
   determining the weights vector x according to $$x \leftarrow \text{diag}(\lfloor h + \lceil Q \rceil x \rfloor) \text{diag}(\lfloor Q \rfloor x)^{-1} x;$$

wherein Q is a matrix whose elements are the inner products of columns of the dose matrix A, $Q \doteq A^T A \in \mathfrak{R}^{m \times n}$, T is a transpose operator, R is a space of real numbers, h is a vector, $h \doteq A^T b \in \mathfrak{R}^m$, diag( ) indicates a diagonal matrix, $\lceil Q \rceil$ is a matrix whose elements are positive elements of the matrix Q, $\lfloor Q \rfloor$ is a matrix whose elements are absolute values of negative elements of the matrix Q.

2. The method of claim 1, wherein the determining the weights vector x comprises:
   multiplying the weights vector x by the matrix $\lceil Q \rceil$ to produce a product $\lceil Q \rceil X$;
   multiplying the weights vector x by the matrix $\lfloor Q \rfloor$ to produce a product $\lfloor Q \rfloor X$;
   forming the vector h of inner products of columns of the matrix A with the target dosage pattern vector b;
   determining a sum of the vector h and the product $\lceil Q \rceil X$;
   dividing the sum element-by-element by the product $\lfloor Q \rfloor X$ to produce a vector of ratios; and multiplying the weights vector x by the vector of ratios to adjust the weights vector x.

3. The method of claim 2, further comprising:

determining the vector ratios iteratively for the adjusted weights vector x until elements of the vector of ratios are close to one.

4. The method of claim 2, further comprising:

determining the vector ratios iteratively for the adjusted weights vector x until changes of elements of weights vector x are close to zero.

5. The method of claim 1, wherein the underdoses and overdoses of the radiation are minimized according to $$\min_x \|Ax - b\|_2^2 \text{ s.t. } x \geq 0,$$

wherein min is a function minimizing of values of the function which is the sum-squared difference between the elements of the optimized dose pattern Ax and the target dose pattern b indicated by a subscript 2.

6. The method of claim 1, wherein the underdoses of radiation are eliminated and overdoses of the radiation are minimized according to a least distance problem (LDP)

$$\min_x \|x\|_2 \text{ s.t. } Ax \geq b, x \geq 0,$$

wherein min is a function minimizing a sum squared error of values of the function indicated by a subscript 2.

7. The method of claim 1, wherein the underdoses of radiation are eliminated and overdoses of the radiation are minimized according to a leas distance problem in a non-negative least squares (NNLS) form $$\min_{u,v} \left\| \begin{bmatrix} A & b \\ I & 0 \end{bmatrix}^T \begin{bmatrix} u \\ v \end{bmatrix} - [0, \ldots, 0, 1]^T \right\|_2^2 \text{ s.t. } u, v \geq 0,$$

wherein min is a function minimizing a sum squared error of values of the Function as indicated by a subscript 2, I is an identity matrix, U, v are positive vectors, and the beam weights vector x is set to $(A^T u - v)/(1 - b^T u)$.

8. A method for optimizing radiation doses delivered by a set of beams, wherein each beam is a radiotherapy particle beam, comprising the steps of:

determining a non-negative beam weights vector x for a dose matrix A indicating a dose delivered to in target voxels by n beams for radiating a target according to a target dosage pattern vector b, such that underdoses and overdoses of the radiotherapy are minimized, wherein the determining comprises:

multiplying the weights vector x by a matrix ⌈Q⌉ whose elements are positive inner products of columns of the dose matrix A to produce a product ⌈Q⌉X;

multiplying the weights vector x by a matrix ⌊Q⌋ whose elements are negated negative inner products of the columns of the dose matrix A to produce a product ⌊Q⌋X;

forming a vector h of inner products of a matrix Q with the target dosage pattern vector b, wherein $Q = A^T A \in \Re^{m \times m}$, T is a transpose operator, R represents a space of real numbers, and $h = A^T b \in \Re^m$;

determining a sum of the vector h and the product ⌈Q⌉X;

dividing the sum by the product ⌊Q⌋X to produce a vector of ratios; and multiplying, the weights vector x by the vector of ratios to adjust the weights vector x, wherein steps of the method are performed by a processor.

9. The method of claim 8, further comprising;

determining the vector ratios iteratively for the adjusted weights vector x until elements of the vector of ratios are close to one.

* * * * *